United States Patent [19]

Jasys

[11] 4,393,001
[45] Jul. 12, 1983

[54] INTERMEDIATES FOR PRODUCTION OF 1,1-DIOXOPENICILLANOYLOXYMETHYL 6-(2-AMINO-2-PHENYLACETAMIDO)-PENICILLANATES

[75] Inventor: Vytautas J. Jasys, New London, Conn.

[73] Assignee: Pfizer Inc., New York, N.Y.

[21] Appl. No.: 427,215

[22] Filed: Sep. 29, 1982

Related U.S. Application Data

[62] Division of Ser. No. 246,456, Mar. 23, 1981, abandoned.

[51] Int. Cl.³ .......................................... C07D 499/32
[52] U.S. Cl. ......................... 260/239.1; 260/245.2 R; 424/271
[58] Field of Search ................................. 260/239.1

[56] References Cited

U.S. PATENT DOCUMENTS

| 4,234,579 | 11/1980 | Barth | 424/246 |
| 4,244,951 | 1/1981 | Bigham | 424/250 |
| 4,325,960 | 4/1982 | Godtfredsen | 424/270 |

FOREIGN PATENT DOCUMENTS 882028 9/1980 Belgium .
2044255 10/1980 United Kingdom .

*Primary Examiner*—Natalie Trousof
*Assistant Examiner*—Vera C. Clarke
*Attorney, Agent, or Firm*—Charles J. Knuth; Albert E. Frost; Paul D. Thomas

[57] ABSTRACT

Compounds of the formula

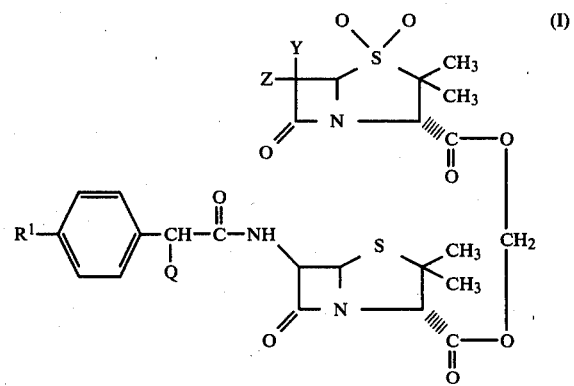

wherein $R^1$ is H or HO; Y and Z are each Cl, Br or I, or Y is H and Z is Cl, Br or I; Q is $N_3$ or $NHCO_2CH_2C_6H_4R^4$ where $R^4$ is H, Cl, Br, $NO_2$, $CH_3$ or $OCH_3$; a process for their use in production of the valuable antibacterial agents 1,1-dioxopenicillanoyloxymethyl 6-(2-amino-2-phenylacetamido)penicillanate and 1,1-dioxopenicillanoyloxymethyl 6-[2-amino-2-(p-hydroxyphenyl)acetamido]-penicillanate, by catalytic hydrogenation in the presence of a noble metal catalyst and novel intermediates useful in preparing said compounds of formula (I).

10 Claims, No Drawings

INTERMEDIATES FOR PRODUCTION OF 1,1-DIOXOPENICILLANOYLOXYMETHYL 6-(2-AMINO-2-PHENYLACETAMIDO)PENICILLANATES

CROSS REFERENCE TO RELATED APPLICATIONS

This is a division of application Ser. No. 246,456 filed Mar. 23, 1981.

BACKGROUND OF THE INVENTION

1. Field of the Invention

The invention relates to novel compounds of formula (I), defined herein, a process for their use in production of 1,1-dioxopenicillanoyloxymethyl 6-(2-amino-2-phenylacetamido)penicillanate antibiotics of formula (II), certain halomethyl (and related) esters of 6-halo (or 6,6-dihalo)penicillanic acid and the corresponding sulfoxides and sulfones useful in preparing compounds of formula (I).

2. Description of the Prior Art

U.S. Pat. No. 4,234,579, issued Nov. 18, 1980, discloses penicillanic acid 1,1-dioxide and esters thereof which are readily hydrolyzable in vivo, their use as antibacterial agents and for enhancing the effectiveness of beta-lactam antibiotics against many beta-lactamase producing bacteria.

U.S. Pat. No. 4,244,951, issued Jan. 13, 1981, discloses novel antibacterial agents of formula (VIII) in which penicillinic acid 1,1-dioxide is linked to known penicillin antibiotics via a methylenedioxo group, i.e.,

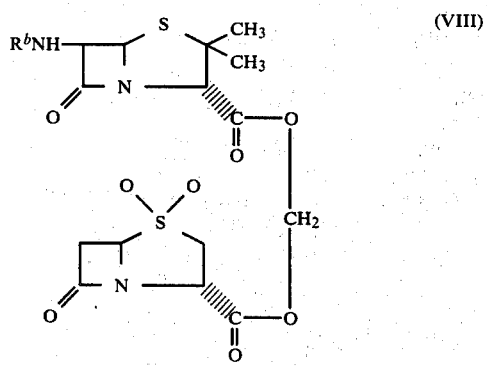

where $R^b$ is the acyl group of a natural or semisynthetic penicillin. Especially preferred values for $R^b$ include 2-amino-2-phenylacetyl and 2-amino-2-(p-hydroxyphenyl)acetyl. The compounds (VIII) are prepared, for example, by reacting a carboxylate salt of the penicillin such as the sodium, potassium or tertiary amine salt with a halomethyl ester (or related ester) of penicillinic acid 1,1-dioxide. The intermediate halomethyl esters are prepared by esterification of penicillanic acid 1,1-dioxide.

Harrison et al., *Journal of the Chemical Society* (London), Perkin I, 1772 (1976) disclose: (a) the oxidation of 6,6-dibromopenicillanic acid with m-chloroperbenzoic acid, to give a mixture of the corresponding alpha- and beta-sulfoxides; (b) oxidation of methyl 6,6-dibromopenicillanate with m-chlorperbenzoic acid to give a methyl 6,6-dibromopenicillanate 1,1-dioxide; (c) oxidation of methyl 6-alpha-chloropenicillanate with m-chloroperbenzoic acid, to give a mixture of the corresponding alpha- and beta-sulfoxides; and (d) oxidation of methyl 6-bromopenicillanate with m-chloroperbenzoic acid, to give a mixture of the corresponding alpha- and beta-sulfoxides.

Clayton, *Journal of the Chemical Society* (London) (C), 2123 (1969), discloses: (a) the preparation of 6,6-dibromo- and 6,6-diiodopenicillanic acid; (b) oxidation of 6,6-dibromopenicillanic acid with sodium periodate, to give a mixture of the corresponding sulfoxides; (c) hydrogenolysis of methyl 6,6-dibromopenicillanate to give methyl 6-alpha-bromopenicillanate; (d) hydrogenolysis of 6,6-dibromopenicillanic acid, and its methyl ester, to give penicillanic acid and its methyl ester, respectively; and (e) hydrogenolysis of a mixture of methyl 6,6-diodopenicillanate and methyl 6-alpha-iodopenicillanate to give pure methyl 6-alpha-iodopenicillanate.

Belgian Pat. No. 882,028, granted Sept. 9, 1980, discloses a process for preparing penicillanic acid 1,1-dioxide and its readily hydrolyzable in vivo esters by oxidation of 6-halopenicillanate or a 6,6-dihalopenicillanate to the corresponding 1,1-dioxide, then dehalogenation to provide the desired penicillanate 1,1-dioxide.

U.S. Pat. No. 3,293,242 discloses 6-(2-azido-2-phenylacetamido)penicillanic acid and salts thereof.

Japan Kokai 78-37,691; *Chem. Abstr.*, 89, 109466v (1978) discloses 6-[2-azido-2-(p-hydroxyphenyl)acetamido]penicillanic acid and its reduction with hydrogen and palladium-on-carbon to give 6-[2-amino-2-(p-hydroxyphenyl)acetamido]penicillanic acid.

SUMMARY OF THE INVENTION

The present invention relates to compounds of the formula

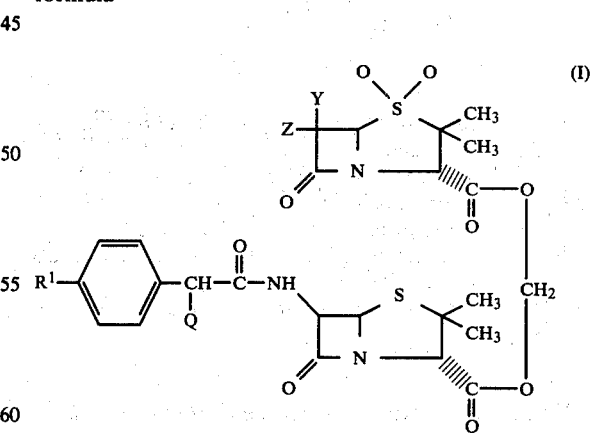

wherein $R^1$ is H or OH; Y and Z are each Cl, Br or I, or Y is H and Z is Cl, Br or I; and Q is $N_3$ or $NHCO_2CH_2C_6H_4R^4$ where $R^4$ is H, Cl, Br, $NO_2$, $CH_3$ or $OCH_3$ useful as intermediates for the production of valuable antibiotics of the formula

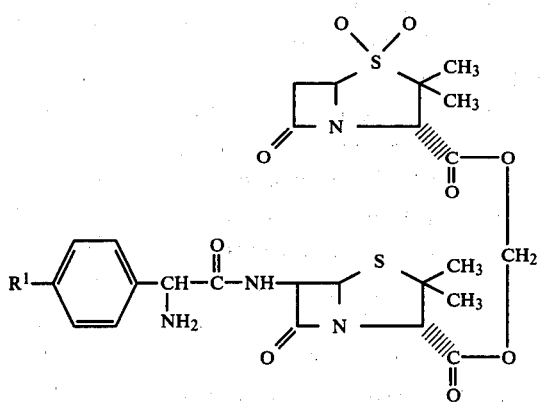

In said compounds of formula (I), the particularly preferred value for Q is $N_3$. Particularly preferred values for Y and Z are Y is H and Z is Br or Cl, or Y and Z are each Cl or Br; especially Y is H, Z is Br or Y and Z are each Br. Most particularly preferred such compounds are those wherein Q is $N_3$, $R^1$ is H or OH, Y and Z are each Br.

The invention also provides a novel process for production of the antibiotics of formula (II) which is characterized by contacting a compound of formula (I) with hydrogen in the presence of a noble metal catalyst and a reaction inert solvent. The invention process has advantages over the prior art in that simultaneously the halogen atoms Y and Z are subjected to hydrogenolysis and the group Q is reduced (when Q is $N_3$) or subjected to hydrogenolysis (when Q is $NHCO_2CH_2C_6H_4R^4$) to produce the antibiotics of formula (II) in a single step. A particularly preferred noble metal catalyst for this process is palladium.

The invention further provides novel intermediates which are useful in preparation of compounds of formula (I). These intermediates are of the formula

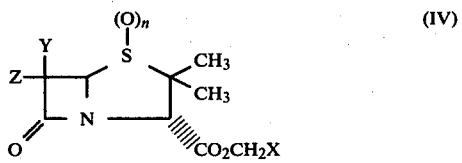

where Y and Z are as defined above for compound (I), n is zero, 1 or 2; and X is Cl, Br, I or $OSO_2R^2$ where $R^2$ is alkyl having from one to six carbon atoms or $C_6H_4R^3$ and $R^3$ is Cl, Br, I, $NO_2$ or alkyl or alkoxy, where each of the latter two groups have from one to three carbon atoms. Particularly preferred intermediates of formula (IV) are those where:

Y is H and Z is Cl or Br, or Y and Z are each Cl or Br;
X is Cl, Br or I; and
n is 0 or 2.

More particularly preferred compounds of formula (IV) are those where:
n is 0, Y is H, Z is Br, or Y and Z are each Br, and X is Cl or I;
n is 2, Y is H, Z is Br, or Y and Z are each Br, and X is I.

Most particularly preferred compounds (IV) are those where:
n is 0, Y and Z are each Br and X is Cl or I;

n is 2, Y and Z are each Br and X is I.

The iodomethyl sulfones of formula (IV) where n is 2 and X is I are especially valuable because of their especially facile coupling with salts of formula (VI) to provide the compounds of formula (I).

DETAILED DESCRIPTION OF THE INVENTION

This invention relates to derivatives of penicillanic acid which is represented by the following structural formula:

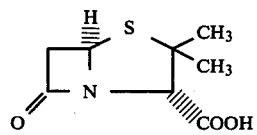

In derivatives of penicillanic acid, broken line attachment (''') of a substituent to the bicyclic nucleus indicates that the substituent is below the plane of the nucleus. Such a substituent is said to be in the alpha-configuration. Conversely, broad line attachment (━) of a substituent to the bicyclic nucleus indicates that the substituent is above the plane of the nucleus. This latter configuration is referred to as the beta-configuration. As used herein a solid line attachment (—) of a substituent to the bicyclic nucleus indicates that the substituent can be in either the alpha-configuration or the beta-configuration.

Compounds of the invention of formulae (I) and (II) are named herein as derivatives of penicillanoyloxymethyl penicillanate. Thus, the compound of formula (I) where $R^1$ is hydrogen and Y and Z are each Br and Q is $N_3$ is designated as 1,1-dioxo-6,6-dibromopenicillanoyloxymethyl 6-(2-azido-2-phenylacetamido)penicillanate.

Additionally, when reference is made herein to a compound which has a 2-Q-2-($R^1$-substituted phenyl)acetamido or 2-amino-2-($R^1$-substituted phenyl)acetamido group at the 6-position of a penicillanic acid derivative, it is understood that this refers to a compound in which said 2-Q-2-($R^1$-substituted phenyl)acetamido or 2-amido-2-($R^1$-substituted phenyl)acetamido has the D-configuration.

In the invention compounds wherein Y is H and Z is Cl, Br or I the Z substituent can be in the alpha-configuration, the beta-configuration or can be a mixture of the two isomers. All such compounds are included in the scope of the invention.

Methods for preparing penicillanoyloxymethyl penicillanates of formula (II) by esterification as illustrated below are disclosed in U.S. Pat. No. 4,244,951 issued Jan. 13, 1981 and Netherlands Patent Application No. 8,000,775 published Aug. 15, 1980, corresponding to British patent application No. 2,044,255:

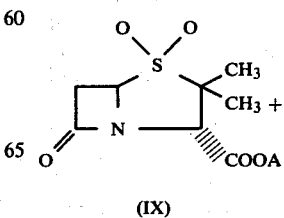

(IX)

-continued

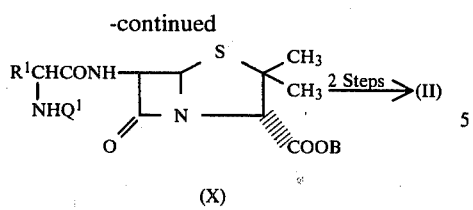

(X)

In the above formulae one of A and B is —$CH_2X^1$ and the other is $M^1$, where $X^1$ is a good leaving group, e.g., Cl, Br, I, $CH_3SO_2O$ or toluenesulfonyloxy; and $M^1$ is a carboxylate salt forming cation, e.g., sodium, potassium, triethylammonium or tetrabutylammonium ion; and $Q^1$ is a conventional amino protecting group, e.g., benzyloxycarbonyl. The initial product obtained is the amino-protected derivative of (II) which affords the desired antibiotic compound upon removal of protecting group Q by standard methods known in the art.

The above-mentioned Netherlands and corresponding British patent applications also disclose a process for preparing the compound of formula (II), where $R^1$ is hydrogen, by coupling chloromethyl 6-(2-azido-2-phenylacetamido)penicillanate and a salt of penicillanic acid 1,1-dioxide, and hydrogenation of the intermediate 1,1-dioxopenicillanoyloxymethyl 6-(2-azido-2-phenylacetamido)penicillanate.

In the prior art methods, the starting 1,1-dioxopenicillanic acid of formula (IX), A=H is obtained e.g. by dehalogenation of the corresponding 6-halo- or 6,6-dihalopenicillanic acid sulfone. The ester (IX), where A is $CH_2X^1$, is obtained from the acid by certain esterification techniques.

Flow Chart A outlines a preferred method for production of the invention compounds of formula (I) and their conversion to antibiotic compounds of formula (II) by simultaneous hydrogenolysis of halogen groups Y and Z and reduction of the azido or $NHCO_2CH_2C_6H_4R^4$ group to $NH_2$ by reaction of compound (I) with hydrogen in the presence of a catalyst.

The starting halopenicillanic acids of formula (III) where M is hydrogen are prepared e.g., from 6-aminopenicillanic acid or the corresponding sulfoxide or sulfone by reaction with nitrous acid and treatment of the resulting 6-diazo compound with a halogen or hydrohalide of formula Y-Z, where Y and Z are as defined above, by methods known in the art. See, e.g., Clayton et al., *Journal of Chemical Society* (London) (C), 2123 (1969).

Flow Chart A

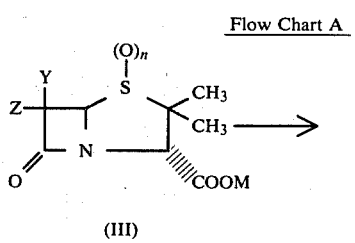

(III)

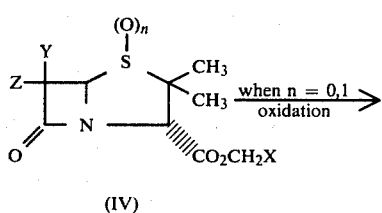

(IV)

-continued
Flow Chart A

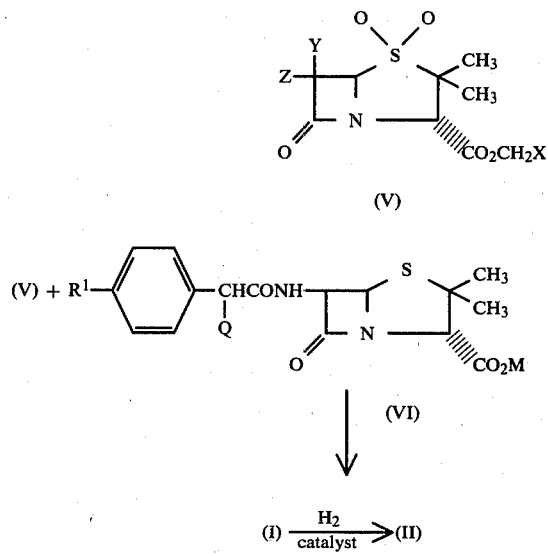

For the esterification step to obtain the compound of formula (IV), the carboxylic acid (III) is converted to a salt wherein M is a cation. A variety of cations can be used to form the carboxylate salt in the compound of formula (III), but salts which are commonly employed include:

alkali metal salts, such as sodium and potassium; alkaline earth metal salts, such as calcium and barium salts; tertiary amine salts, such as trimethylamine, triethylamine, tributylamine, N-methylmorpholine and N-methylpyrrolidine; and tetraalkyl ammonium salts such as tetramethylammonium, tetraethylammonium, dimethyl diisopropylammonium, tetrabutylammonium and diethyl di-n-hexylammonium salts. Particularly preferred such salts are the sodium, potassium and tetrabutylammonium salts.

The salt of formula (III) is reacted with a compound of the formula $X^2CH_2X$, wherein X is as defined above and $X^2$ is X or a better leaving group than X, e.g., when X is Cl, $X^2$ may be Cl, Br, I, $OSO_2Cl$, $OSO_2CH_3$ or p-$CH_3C_6H_4SO_2O$. Particularly preferred values for $X^2$ are I and $OSO_2Cl$.

The reaction between $X^2CH_2X$ and the salt of formula (III) is usually carried out by contacting approximately equimolar amounts of the reactants in a polar, organic solvent, at a temperature in the range of from about $-10°$ to $80°$ C. and preferably from about $0°$ to $60°$ C. The reaction is ordinarily complete in from a few hours to a few days. The desired ester of formula (IV) is isolated by methods well known in the art. For example, by evaporation of solvent and purification of the crude product, if desired, e.g., by column chromatography.

Examples of suitable polar solvents which can be employed in this reaction are dimethylformamide, N-methylpyrrolidone, dimethylsulfoxide, ethyl acetate, dichloromethane, acetone and hexamethylphosphoric triamide; alternately, an excess of the reagent $X^2CH_2X$ e.g., $ICH_2Cl$, can serve as solvent.

In the next step of this method, the compounds of formula (IV) where n is zero or one are oxidized to the corresponding sulfone of formula (V). While any of the oxidizing agents known in the art for oxidation of sulfides to sulfones may be employed in this step, preferred oxidizing agents are sodium permanganate, potassium permanganate, calcium permanganate, hydrogen peroxide in the presence of certain transition metal catalysts, peractic acid or m-chloroperbenzoic acid. The oxidation is carried out in the presence of a reaction inert solvent, preferably at a temperature of from about −30° to 60° C.

Particularly preferred oxidizing agents are hydrogen peroxide in the presence of certain transition metal catalysts, potassium permanganate and m-chloroperbenzoic acid. Especially preferred are potassium permanganate and m-chloroperbenzoic acid.

When a compound of the formula (IV), as defined above, is oxidized to the corresponding compound of the formula (V), using a metal permanganate, the reaction is usually carried out by treating the compound of the formula (IV) with from about two to about ten molar equivalents, and preferably from about two to four molar equivalents, of the permanagnate in an appropriate, reaction-inert solvent system.

When said compound of formula (IV) is a sulfoxide, wherein n is 1 is employed in this step, approximately half of the above amount of oxidant is ordinarily employed.

An appropriate, reaction-inert solvent system is one that does not adversely interact with either the starting materials or the product, and water is commonly used. If desired, a co-solvent which is miscible with water but will not interact with the permanganate such as e.g., tetrahydrofuran or acetone can be added. The reaction can be carried out at a temperature in the range from about −30° to about 60° C., and it is preferably carried out at about 10° to about 30° C. At about room temperature the reaction is normally substantially complete within a short period, e.g. within two hours. Although the reaction can be carried out under neutral, basic or acid conditions, it is preferable to operate at a pH in the range from about 4 to about 9. However, it is essential to choose conditions which avoid decomposition of the beta-lactam ring system of the compounds of formulae (IV) or (V). The product is recovered by conventional techniques. Any excess permanganate is usually decomposed using sodium bisulfite, and then if the product is out of solvent, it is recovered by filtration. It is separated from manganese dioxide by extracting it into an organic solvent and removing the solvent by evaporation. Alternatively, if the product is not out of solution at the end of the reaction, it is isolated by the usual procedure of solvent extraction.

When a compound of the formula (IV) wherein n is zero is oxidized to the corresponding compound of the formula (V) using a peroxycarboxylic acid, e.g. m-chloroperbenzoic acid, the reaction is usually carried out by treating the compound of the formula (V) with from about 2 to about 6 molar equivalents, and preferably about 2.2 molar equivalents of the oxidant in a reaction-inert organic solvent. As above, only half the amount of oxidant is ordinarily required when sulfoxides of formula (IV) are employed. Preferred reaction-inert solvents are chlorinated hydrocarbons, such as dichloromethane, chloroform and 1,2-dichloroethane; ethers, such as diethyl ether, tetrahydrofuran and 1,2-dimethoxyethane; and ethyl acetate. The reaction is normally carried out at a temperature of from about −30° to about 50° C., and preferably from about −15° to about 30° C. At about 0° C., reaction times of about 4 to about 16 hours are commonly used. The product of formula (V) is isolated by standard methods, e.g., decomposition of excess oxidant by addition of sodium bisulfite, partitioning the reaction mixture between water and water-immiscible solvent and evaporation of solvent from the washed extract. The crude product can be purified, e.g., by chromatography on silica gel.

When hydrogen peroxide in the presence of certain transition metal catalysts is employed to oxidize a sulfide or sulfoxide such as the compounds of formula (IV) wherein n is zero or 1 to the corresponding sulfone of formula (V), preferred transition metal catalysts are inorganic compounds of tungsten, molybdenum or zirconium in which the metals are in their highest oxidation state. Examples of such compounds are tungstic acid, sodium tungstate, zirconium tetrachloride, molybdic acid and potassium molybdate. The transition metal catalysts can be carried out over a pH range of about 3 to 9, however a pH of from about 4 to 7 is preferred. When the compound to be oxidized is a sulfide, such as that of formula (IV) where n is zero, at least two moles of hydrogen peroxide per mole of said sulfide is required to provide the corresponding sulfone. However, for oxidizing sulfoxides to sulfones or sulfides to sulfoxides, only one mole of hydrogen peroxide is required to afford the desired product. Preferred reaction inert solvents for the oxidation with hydrogen peroxide/transition metal catalyst include the lower alkanols such as methanol, ethanol and isopropanol; ethylene glycol, ethyl acetate, 1,2-dimethoxyethane, water and mixtures thereof. While the oxidation can be carried out over a wide range of temperature, a preferred temperature is in the range from about 20° to 60° C., at which temperature the oxidation is ordinarily complete in from about two hours to two days, e.g., overnight. The desired product is then isolated and can be purified, if desired, by methods described above and in the Examples.

The reaction of the intermediates (V) with the 6-(2-Q-substituted-2-phenylacetamido)penicillanate salts of formula (VI) where M is as previously defined for compound (III), to provide the invention compounds of formula (I) is usually carried out by contacting the reactants in a polar, organic solvent at a temperature in the range from about 0° C. to about 80° C. and preferably from 25° to 50° C. The compounds of formula (V) and (VI) are usually contacted in substantially equimolar proportions, but an excess of either reagent, for example up to a ten-fold excess, can be used. A wide variety of solvents can be used, but it is usually advantageous to use a relatively polar solvent, since this has the effect of speeding up the reaction. Typical solvents which can be used include N,N-dimethylformamide, N,N-dimethylacetamide, N-methylpyrrolidone, dimethylsulfoxide, ethyl acetate, dichloromethane, acetone and hexamethylphosphoric triamide. The reaction time varies according to a number of factors, but at about 25° C. reaction times of several hours, e.g. 12 to 24 hours, are commonly used.

The compound of formula (I) is isolated in conventional fashion. When a water-miscible solvent is used, it is usually sufficient simply to dilute the reaction medium with an excess of water. The product is then extracted into a water immiscible solvent such as ethyl acetate, and then the product is recovered by solvent evaporation. When a water immiscible solvent is used, it is usually sufficient to wash the solvent with water, and then recover the product by solvent evaporation. The compound of formula (I) can be purified by well-known methods, such as recrystallization or chromatography, but due regard must be given to the lability of the beta-lactam ring system.

A particularly preferred method for production of compounds of formula (I) from a compound of formula (III) is outlined below.

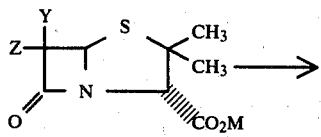

(III, n = 0)

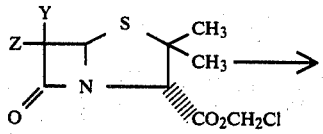

(IV, n = 0, X = Cl)

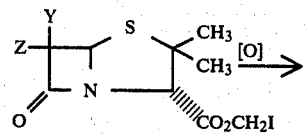

(IV, n = 0, X = I)

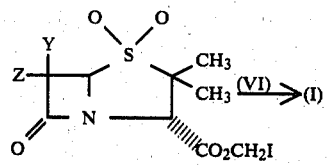

(V, X = I)

In the initial step of the particularly preferred method the sulfide, (III, n=0), wherein M, Y and Z are as previously defined, is reacted with a compound of the formula $X^2CH_2Cl$ where $X^2$ is as defined above, e.g., $ICH_2Cl$, employing methods and conditions defined previously for the preferred method employing $X^2CH_2X$.

In the second step of this method the chloromethyl ester is converted to the corresponding iodomethyl ester (IV, n=0, X=I), for example by contacting it with at least an equimolar amount of an alkali metal iodide, alkaline earth metal iodide or ammonium iodide in the presence of a reaction inert polar solvent. Examples of suitable solvents for this reaction are dimethylformamide, N-methylpyrrolidone, dimethyl sulfoxide, methanol, ethanol, ethyl acetate, acetone and methylethyl ketone. A preferred solvent is acetone. While the reaction can be carried out successfully over a wide range of temperature, a temperature in the range of about 0° to 50° C., and especially 20° to 40° C. is preferred. Within the latter range of temperature the reaction is ordinarily complete in from about 1 to 20 hours. The desired product of formula (IV, n=0, X=I), is then isolated and purified by methods well known to those of skill in the art. For example, the solvent is evaporated, the residue partitioned between water and a water-immiscible solvent, e.g. ethyl acetate. Evaporation of solvent then affords the product which can be purified, if desired, e.g., by chromatography on silica gel.

In the next step of this especially preferred method the iodomethyl ester of formula (IV, n=0, X=I) is oxidized to the corresponding sulfone of formula (V, X=I) employing one of the above preferred oxidizing agents described above, under the preferred conditions, also described above.

The iodomethyl ester (V, X=I) is then coupled with a compound of formula (VI) as described above, to provide the invention compounds of formula (I).

At least two moles of hydrogen peroxide per mole of said sulfide is required to provide the corresponding sulfone.

An alternate method for preparation of the iodomethyl sulfone (V, X=I) involves oxidation of the chloromethyl ester of formula (IV, n=0, X=Cl) or, e.g., the corresponding sulfone employing the above oxidants and conditions; and subsequent conversion of, e.g. the chloromethyl sulfone to the iodomethyl sulfone (V) by reaction with iodide salt, also as described above. However, the latter step with iodide salt, e.g. NaI in acetone, with compounds wherein both of Y and Z are halogen can result in partial dehalogenation at the 6-position of the sulfone to afford a mixture containing iodomethyl 6-alpha-halopenicillanate 1,1-dioxide as well as the desired 6,6-dihalo compound of formula (V, X=I).

An alternate method for obtaining the valuable intermediates of formula (I) involves reaction of a compound of formula (XI) with a compound of formula (XII) as illustrated below

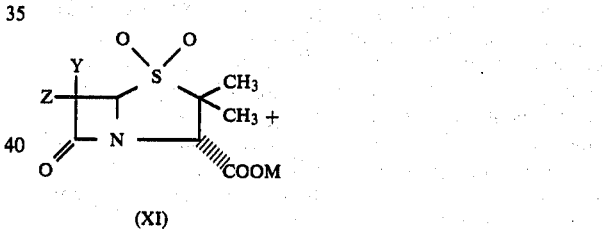

(XI)

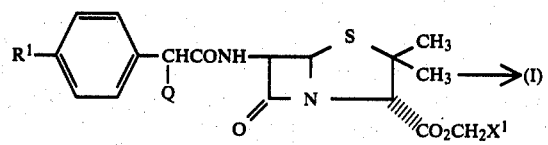

(XII)

wherein $R^1$, M, Q, $X^1$, Y and Z are as previously defined, employing the same procedure and conditions described above for the coupling reaction with compounds of formulae (V) and (VI).

The compounds of formula (I) are useful intermediates for production of the valuable antibiotic compounds of formula (II), disclosed in U.S. Pat. No. 4,244,951.

While various methods can be employed for conversion of intermediates of formula (I) to the antibiotics of formula (II), a particularly convenient and preferred method is the simultaneous hydrogenolysis of halogen groups Y and Z as defined above and reduction of the azido or benzyloxycarbonylamino group Q, as defined above, to $NH_2$ by means of hydrogen in the presence of a noble metal catalyst. A particularly convenient method for carrying out this simultaneous hydrogenolysis and reduction is to stir or shake a solution of a compound of the formula (I) under an atmosphere of hydrogen, or hydrogen mixed with an inert diluent such as nitrogen or argon, in the presence of a noble metal hydrogenation catalyst, and a reaction inert solvent. Suitable solvents for this hydrogenation reaction are those which substantially dissolve the starting compound of the formula (I) but which do not themselves suffer hydrogenation or hydrogenolysis. Examples of such solvents include lower alkanols such as methanol, ethanol and isopropanol; ethers such as diethyl ether, tetrahydrofuran, dioxan and 1,2-dimethoxyethane; low molecular weight esters such as ethyl acetate and butyl acetate; tertiary amides such as N,N-dimethylformamide, N,N-dimethylacetamide and N-methylpyrrolidone; methylene chloride and mixtures thereof.

Additionally, it is often desirable to carry out this reaction in the presence of a sufficient amount of an acid binding agent to bind one or both molar equivalents of hydrogen halide formed. Examples of suitable acid binding agents include sodium bicarbonate, calcium carbonate, trisodium phosphate, potassium citrate and tertiary amines such as triethylamine, N,N-dimethylaniline, N-methylmorpholine, N-methylpiperidine, N,N'-dimethylpiperazine and the like. Introduction of the hydrogen gas into the reaction medium is usually accomplished by carrying out the reaction in a sealed vessel, containing the compound of formula (I), the solvent, the catalyst and the hydrogen. The pressure inside the reaction vessel can vary from about 1 to about 100 kg./cm.$^2$. The preferred pressure range, when the atmosphere inside the reaction vessel is substantially pure hydrogen, is from about 2 to about 5 kg./cm.$^2$. The reaction with hydrogen is generally run at a temperature of from about 0° to about 60° C., and preferably from about 25° to about 50° C. Utilizing the preferred temperature and pressure values, hydrogenolysis of halogens and reduction of the group Q generally takes place in a few hours, e.g., from about 2 hours to about 20 hours. The preferred noble metal catalysts used in this hydrogenation reaction are the type of agents known in the art for this kind of transformation, for example, nickel, palladium, platinum and rhodium. Palladium is particularly preferred. The catalyst is usually present in an amount from about 0.1 to about 25 weight-percent, and preferably from about 1 to about 10 weight-percent, based on the compound of formula (I). It is often convenient to suspend the catalyst on an inert support; one particularly convenient catalyst is palladium suspended on an inert support such as carbon. Another convenient catalyst is palladium-on-calcium carbonate in which the calcium carbonate serves as a support for the noble metal and as acid binding agent.

When the hydrogenolysis and reduction is substantially complete, the desired antibiotic of formula (II) is then isolated by standard methods, e.g., the catalyst is removed by filtration, the solvent evaporated and the product purified, if desired, by well known methods such as crystallization or by chromatography.

Alternatively, the product of formula (II) can be isolated in the form of a pharmaceutically acceptable acid addition salt, for example by treating filtrate obtained upon removal of catalyst or a solution of the isolated free base with an equivalent amount of a pharmaceutically acceptable acid and removal of solvent, e.g. by filtration or evaporation. Examples of pharmaceutically acceptable acids which may be employed include hydrochloric, hydrobromic, sulfuric, phosphoric, acetic, maleic, fumaric, succinic, lactic, tartaric, citric, gluconic, saccharic and p-toluenesulfonic acids.

It should also be noted that the hydrochloride, hydrobromide, hydroiodide salt or mixtures thereof of compounds of formula (II) is obtained directly from the hydrogenation mixture if one employs only one molar equivalent of acid binding agent for the starting materials of formula (I) wherein each of Y and Z are Cl, Br or I, or no acid binding agent is employed for starting materials of formula (I) wherein Y is H and Z is Cl, Br or I.

As mentioned above the compounds of formula (I) are useful intermediates for preparation of antibacterial agents of formulae (II) and (VIII) disclosed in U.S. Pat. No. 4,244,951 and British Patent Application No. 2,044,255.

The compounds of formula (II) and (VIII) possess in vivo antibacterial activity in mammals, and this activity can be demonstrated by standard techniques for penicillin compounds. For example, the compound of formula (II) is administered to mice in which acute infections have been established by intraperitoneal inoculation with a standardized culture of a pathogenic bacterium. Infection severity is standardized such that the mice receive one to ten times the $LD_{100}$ ($LD_{100}$: the minimum inoculation required to consistently kill 100 percent of control mice). At the end of the test, the activity of the compound is assessed by counting the number of survivors which have been challenged by the bacterium and also have received the compound of formula (II). The compounds of formula (II) can be administered by both the oral (p.o.) and subcutaneous (s.c.) route.

The in vivo activity of the antibacterial compounds (II) and (VIII) make them suitable for the control of bacterial infections in mammals, including man, by both the oral and parenteral modes of administration. The compounds are useful in the control of infections caused by susceptible bacteria in human subjects. In general, it is the substituent $R^b$ which determines whether a given bacterium will be susceptible to a given compound of formula (VIII). A compound of formula (VIII) breaks down to the corresponding compound of formula (VII) (or salt thereof) and penicillanic acid 1,1-dioxide (XIII) after administration to a mammalian subject by either the oral or parenteral route.

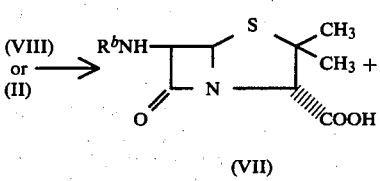

(VII)

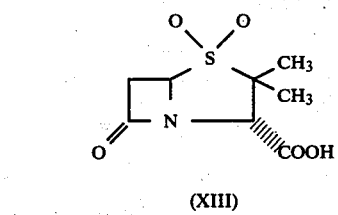

(XIII)

Penicillanic acid 1,1-dioxide then functions as a beta-lactamase inhibitor, and it increases the antibacterial effectiveness of the compound of formula (VII) (or salt thereof). When $R^b$ is D-2-amino-2-phenylacetyl or D-2- amino-2-[4-hydroxyphenyl]acetyl the compounds are useful in the control of infections caused by susceptible strains of *Escherichia coli* and *Staphylococcus aureus*.

In determining whether a particular strain of *Staphylococcus aureus* or *Escherichia coli* is sensitive to a particular compound of formulae (II) and (VIII), the in vivo test described earlier can be used. Alternatively, the minimum inhibitory concentration (MIC) of a 1:1 mixture of the compound of formula (VII) (or its salt) and the compound of formula (XIII) (or its salt) can be measured. The MIC's can be measured by the procedure recommended by the International Collaborative Study on Antibiotic Sensitivity Testing (Ericcson and Sherris, *Acta. Pathologica et Microbiologia* Scandinav, Supp. 217, Section B: 64-68 [1971]), which employs brain heart infusion (BHI) agar and the inocula replicating device. Overnight growth tubes are diluted 100 fold for use as the standard inoculum (20,000-10,000 cells in approximately 0.002 ml. are placed on the agar surface; 20 ml. of BHI agar/dish). Twelve 2 fold dilutions of the test compound are employed, with initial concentration of the test drug being 200 mcg./ml. Single colonies are disregarded when reading plates after 18 hrs. at 37° C. The susceptibility (MIC) of the test organism is accepted as the lowest concentration of compound capable of producing complete inhibition of growth as judged by the naked eye.

When using an antibacterial compound of formula (II), or a salt thereof, in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the oral mode of administration, the antibacterial compound (II) can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous, and intravenous use, sterile solutions of the active ingredient are usually prepared, and the pH of the solutions are suitably adjusted and buffered. For intravenous use, the total concentration of solutes should be controlled to render the preparation isotonic.

The antibacterial compounds of formula (II) and pharmaceutically acceptable salts thereof are of use in human subjects and the daily dosages to be used will not differ significantly from other, clinically-used, penicillin antibiotics. The prescribing physician will utimately determine the appropriate dose for a given human subject, and this can be expected to vary according to the age, weight, and response of the individual patient as well as the nature and the severity of the patient's symptoms. The compounds (II) will normally be used orally at dosages in the range from about 20 to about 100 mg. per kilogram of body weight per day, and parenterally at dosages from about 10 to about 100 mg. per kilogram of body weight per day, usually in divided doses. In some instances it may be necessary to use doses outside these ranges.

The following examples and preparations are provided solely for further illustration. Infrared (IR) spectra were measured neat, as nujol mulls, or as potassium bromide discs (KBr discs) and diagnostic absorption bands are reported in wave numbers (cm$^{-1}$). Nuclear magnetic resonance spectrum (NMR) were measured at 60 MHz for solutions in deuterated chloroform (CDCl$_3$), D$_2$O, CD$_3$SOCD$_3$, or deuterated acetone (CD$_3$COCD$_3$), and peak positions are reported in parts per million downfield from tetramethylsilane. The following abbreviations for peak shapes are used: s, singlet; d, doublet; t, triplet; q, quartet; m, multiplet; dd, double doublet.

EXAMPLE 1

Chloromethyl 6,6-dibromopenicillanate 6,6-Dibromopenicillanic acid (8.0 g., 22 mmole) was stirred with 75 ml. methylene chloride, 35 ml. water was added. To this was added tetrabutylammonium hydroxide to adjust to pH 8. The organic layer was separated, the aqueous phase extracted with 30 ml. methylene chloride. The combined organic layers were evaporated to dryness in vacuo to provide the tetrabutylammonium salt of 6,6-dibromopenicillanic acid, 14.2 g., as a light brown oil. To this was added 40 ml. of chloroiodomethane, and the resulting mixture stirred under nitrogen for three hours at room temperature. The reaction mixture was concentrated in vacuo, the residue stored overnight at room temperature and purified by chromatography on 300 g. silica gel, eluting with 95:5 (by volume) toluene/ethyl acetate. Fractions containing the less polar material were combined and evaporated to afford 5.4 g. (59%) of the desired product, M.P. 105°-106° C. $^1$H-NMR (CDCl$_3$) ppm (delta): 1.6 (s, 3H), 1.75 (s, 3H), 4.62 (s, 1H), 5.8 (dd, 2H), 5.82 (s, 1H).

When the above procedure is repeated, except that the chloroiodomethane used therein is replaced by an equimolar amount of bromoiodomethane, diiodomethane, di(methylsulfonyloxy)methane, di(isobutylsulfonyloxy)methane, di(n-hexylsulfonyloxy)methane, di(benzenesulfonyloxy)methane or a compound of the formula (R$^2$C$_6$H$_4$SO$_2$O)$_2$CH$_2$ where R$^2$ is 4-Cl, 2-Br, 4-I, 3-NO$_2$, 4-CH$_3$, 3-(CH$_3$)$_2$CH, 4-CH$_3$O, 3-C$_2$H$_5$O or 4-n-C$_3$H$_7$O, this affords, respectively:
bromomethyl 6,6-dibromopenicillanate,
iodomethyl 6,6-dibromopenicillanate,
methylsulfonyloxymethyl 6,6-dibromopenicillanate,
isobutylsulfonyloxymethyl 6,6-dibromopenicillanate,
n-hexylsulfonyloxymethyl 6,6-dibromopenicillanate,
benzenesulfonyloxymethyl 6,6-dibromopenicillanate,
and R$^2$-C$_6$H$_4$-sulfonyloxymethyl 6,6-dibromopenicillanates where R$^2$ is as defined above for the di(substituted phenylsulfonyloxy)methane reagent.

EXAMPLE 1A

Iodomethyl 6,6-dibromopenicillanate

To 25 ml. of acetone was added 4.15 g. (10.2 mmole) chloromethyl 6,6-dibromopenicillanic acid and 7.5 g. (50 mmole) sodium iodide. The mixture was stirred overnight at room temperature and the acetone was evaporated to afford a dark residue. This was dissolved in 150 ml. ethyl acetate, washed with water (3×25 ml.), saturated brine (25 ml.), dried (MgSO$_4$) and the solvent evaporated in vacuo to yield a residual oil which was purified by chromatography on 100 g. silica gel, eluting with 1:1 (by volume) ethyl acetate/hexane. Thirty milliliter fractions were collected. The product eluted in fractions 4–6, which were combined and evaporated to afford 5.95 g. of colorless oil which crystallized upon standing, M.P. 67°–68° C. $^1$H-NMR (CDCl$_3$) ppm (delta): 1.55 (s, 3H), 1.65 (s, 3H), 4.54 (s, 1H), 5.8 (s, 1H), 5.98 (s, 2H).

Employing bromomethyl 6,6-dibromopenicillanate, bromomethyl 6,6-dichloropenicillanate, chloromethyl 6,6-dichloropenicillanate, chloromethyl 6-bromo-6-chloropenicillanate, chloromethyl 6-chloro-6-iodopenicillanate, chloromethyl 6-bromo-6-iodopenicillanate or bromomethyl 6-bromo-6-iodopenicillanate in place of chloromethyl 6,6-dibromopenicillanate in the above procedure provides the corresponding iodomethyl ester, in each case.

EXAMPLE 1B

Employing the appropriate 6-substituted or 6,6-disubstituted penicillanic acid in the procedures of Example 1 and 1A, the following esters are prepared in like manner.

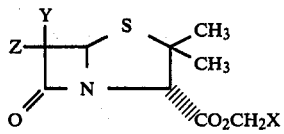

| Y | Z | X |
|---|---|---|
| H | alpha-Br | I |
| H | alpha-Cl | CH$_3$SO$_2$O |
| H | alpha-I | C$_2$H$_5$SO$_2$O |
| H | beta-Cl | (CH$_3$)$_2$CHCH$_2$SO$_2$O |
| H | beta-Br | Cl |
| H | beta-I | C$_6$H$_5$SO$_2$O |
| Cl | Cl | 4-CH$_3$C$_6$H$_4$SO$_2$O |
| Cl | Cl | Cl |
| Br | Cl | Cl |
| Cl | I | n-C$_6$H$_{13}$SO$_2$O |
| Cl | I | Cl |
| Br | I | Cl |
| Br | I | CH$_3$SO$_2$O |
| Br | Br | Br |
| I | I | Cl |
| Br | Br | 4-CH$_3$C$_6$H$_4$SO$_2$O |
| Cl | I | 4-ClC$_6$H$_4$SO$_2$O |
| Br | I | 4-CH$_3$OC$_6$H$_4$SO$_2$O |
| I | I | I |
| Cl | Cl | 2-BrC$_6$H$_4$SO$_2$O |
| Cl | Br | 4-IC$_6$H$_4$SO$_2$O |
| Cl | Cl | 3-NO$_2$C$_6$H$_4$SO$_2$O |
| Cl | Cl | 3-(CH$_3$)$_2$CHC$_6$H$_4$SO$_2$O |
| Br | Br | 3-C$_2$H$_5$OC$_6$H$_4$SO$_2$O |
| Cl | I | 4-n-C$_3$H$_7$OC$_6$H$_4$SO$_2$O |

EXAMPLE 2

Chloromethyl 6,6-dibromopenicillanate 1,1-Dioxide

A solution of 7.1 g. (17.4 mmole) chloromethyl 6,6-dibromopenicillanate in 75 ml. ethyl acetate was cooled to 0° C. and 7.3 g. (36 mmole) of m-chloroperbenzoic acid was added. The mixture was stirred under nitrogen at 0° C. overnight, diluted to 150 ml. with ethyl acetate, and 50 ml. water added at 0° C. Sufficient sodium bisulfite was added to destroy the excess peracid, the mixture adjusted from pH 2 to pH 7.5 with sodium bicarbonate, the organic layer separated and washed with 50 ml. saturated sodium bicarbonate, 50 ml. water and 25 ml. brine. The washed extracts were dried (MgSO$_4$), concentrated to dryness in vacuo and the residue purified by chromatography on 300 g. silica gel, eluting with 9:1 (by volume) toluene/hexane to afford 5.0 g. (65%) of the desired dioxide as a crystalline solid, M.P. 95°–96° C. $^1$H-NMR (CDCl$_3$) ppm (delta): 1.5 (s, 3H), 1.7 (s, 3H), 4.58 (s, 1H), 5.04 (s, 1H), 5.8 (dd, 2H).

Analysis: Calculated for C$_9$H$_{10}$NO$_5$SBr$_2$Cl: C, 24.59; H, 2.29; N, 3.18. Found: C, 24.63; H, 2.49; N, 3.31.

A second, more polar component was isolated from the chromatography column, 0.8 g. This was identified as a 9:1 mixture of the alpha- and beta-sulfoxides of chloromethyl 6,6-dibromopenicillanate by $^1$H-NMR.

EXAMPLE 2A

Iodomethyl 6,6-dibromopenicillanate 1,1-Dioxide

To 40 ml. of acetone was added 0.25 g. (0.5 mmole) iodomethyl 6,6-dibromopenicillanate and the mixture stirred until a solution was obtained, water, 10 ml., was added followed by sufficient concentrated phosphoric acid to adjust the mixture to pH 4.0. Then 158 mg. (1 mmole) powdered potassium permanganate was added and the mixture stirred at room temperature for 1.25 hours. Ethyl acetate, 100 ml. and water, 50 ml., were added. The resulting mixture adjusted to pH 2.0 with 6 N hydrochloric acid and sodium bisulfite added to consume the excess oxidizing agent (pH 2.9). The organic layer was separated, the aqueous phase extracted with 50 ml. ethyl acetate and the combined organic layers were washed with saturated brine (3×25 ml.). After drying over anhydrous sodium sulfate and evaporation of solvent, 0.29 g. of colorless oil was obtained. The oil was purified by chromatography on 25 g. of silica gel eluting with 1:1 ethyl acetate/hexane taking 15 ml. fractions. Fractions 4 and 5 were combined and evaporated in vacuo to yield 0.27 g. (100%) of colorless oil which crystallized upon standing, M.P. 71°–73° C. $^1$H-NMR (CDCl$_3$) ppm (delta): 1.5 (s, 3H), 1.62 (s, 3H), 4.49 (s, 1H), 5.02 (s, 1H), 5.98 (dd, 2H).

Use of an equivalent amount of sodium permanganate or calcium permanganate in place of potassium permanganate in the above procedure afforded the same product in like manner.

Attempts to prepare iodomethyl 6,6-dibromopenicillanate 1,1-dioxide from the chloromethyl ester prepared in Example 2, by treatment with sodium iodide in acetone by the procedure of Example 1A gave iodomethyl 6-alpha-bromopenicillanate 1,1-dioxide. $^1$H-NMR (CDCl$_3$) ppm/delta: 1.55 (s, 3H), 1.70 (s, 3H), 4.43 (s, 1H), 5.2 (d, 1H), 5.75 (d, 1H), 6.0 (dd, 2H).

EXAMPLE 3

Iodomethyl 6-bromo-6-chloropenicillanate 1,1-Dioxide

A solution of 7.6 g. (17.4 mmole) iodomethyl 6-bromo-6-chloropenicillanate in 75 ml. ethyl acetate was cooled to 0° C. and 7.3 g. (36 mmole) of m-chloroperbenzoic acid was added. The mixture was stirred under nitrogen at 0° C. overnight, diluted to 150 ml. with ethyl acetate, and 50 ml. water added at 0° C. Sufficient sodium bisulfite was added to destroy the excess peracid, the mixture adjusted from pH 2 and to pH 7.5 with sodium bicarbonate, the organic layer separated and washed with 50 ml. saturated sodium bicarbonate, 50 ml. water and 25 ml. brine. The washed extracts were dried (MgSO4), concentrated to dryness in vacuo and the residue purified by chromatography on silica gel.

EXAMPLE 4

Iodomethyl 6,6-dichloropenicillanate 1,1-Dioxide

To a solution of 4.09 g. (0.01 mole) iodomethyl 6,6-dichloropenicillanate in 50 ml. acetone is added 2.5 ml. (0.24 mole) 30% hydrogen peroxide and 1 ml. of 0.5 M aqueous sodium tungstate. The mixture is heated at reflux for one hour and allowed to stir overnight at room temperature. Evaporation of solvent affords the crude product which is purified by chromatography on silica gel.

When aqueous potassium molybdate or zirconium tetrachloride is used in place of sodium tungstate in the above procedure the result is substantially the same.

When methanol, ethanol, isopropanol, methylethyl ketone or their mixtures with water are employed as solvent in place of acetone and the reaction is carried out at from 25° to 60° C., the title compound is obtained in like manner.

EXAMPLE 5

Employing the compounds provided in Example 1B as starting materials in the procedures of Example 2 through 4 provides the corresponding compound of the formula below

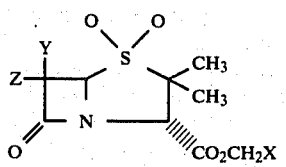

where Y, Z and X are as defined in Example 1B.

EXAMPLE 6

Chloromethyl 6-beta-bromopenicillanate 1,1-Dioxide

To a solution of 3.52 g. (8 mmole) chloromethyl 6,6-dibromopenicillanate 1,1-dioxide in dry benzene (100 ml.), under nitrogen, is added at 0° C., 2.32 g. (8 mmole) tri-n-butyltin hydride. The resulting mixture is stirred overnight at room temperature, the solvent evaporated in vacuo and the residue purified by column chromatography on silica gel to provide the title compound.

Alternately, the same product is obtained by employing chloromethyl 6,6-dibromopenicillanic acid in the above procedure and oxidizing the resulting sulfide, chloromethyl 6-beta-bromopenicillanate, to the sulfone by the procedures of Example 2, 2A, 3 or 4.

EXAMPLE 7

Iodomethyl 6-beta-bromopenicillanate 1,1-Dioxide

A solution of 0.12 g. (0.33 mmole) chloromethyl 6-beta-bromopenicillanate 1,1-dioxide and 0.25 g. (1.66 mmole) sodium iodide in 5 ml. of acetone was stirred 30 hours at room temperature. The resulting pale yellow suspension was evaporated to dryness and the residue taken up in 50 ml. of ethyl acetate, washed successively with 2×10 ml. water, 10 ml. saturated brine and dried over anhydrous sodium sulfate. The resulting solution was evaporated at reduced pressure to obtain the title compound, as a solid, 0.14 g. $^1$H-NMR (CDCl$_3$) ppm (delta)-1.45 (s, 3H), 1.65 (s, 3H), 4.5 (s, 1H), 4.83 (d, 1H), 5.42 (d, 1H), 6.0 (dd, 2H).

EXAMPLE 8

6-alpha-Bromopenicillanic Acid 1,1-Dioxide

To a stirred mixture of 560 ml. of water, 300 ml. of dichloromethane and 56.0 g. of 6-alpha-bromopenicillanic acid was added 4 N sodium hydroxide solution until a stable pH of 7.2 was achieved. This required 55 ml. of sodium hydroxide. The mixture was stirred at pH 7.2 for 10 minutes and then it was filtered. The layers were separated and the organic phase was discarded. The aqueous phase was then poured rapidly, with stirring, into an oxidizing mixture which had been prepared as follows.

In a 3 liter flask was mixed 63.2 g. of potassium permanganate, 1,000 ml. of water and 48.0 g. of acetic acid. This mixture was stirred for 15 minutes at 20° C. and then it was cooled to 0° C.

After the 6-alpha-bromopenicillanic acid solution had been added to the oxidizing mixture, a cooling bath at $-15°$ C. was maintained around the reaction mixture. The internal temperature rose to 15° C. and then fell to 5° C. over a 20 minute period. At this point, 30.0 g. of sodium metabisulfite was added with stirring over a 10 minute period at about 10° C. After a further 15 minutes, the mixture was filtered, and the pH of the filtrate was lowered to 1.2 by the addition of 170 ml. of 6 N hydrochloric acid. The aqueous phase was extracted with chloroform, and then with ethyl acetate. Both the chloroform extracts and the ethyl acetate extracts were dried using anhydrous magnesium sulfate and then they were evaporated in vacuo. The chloroform solution afforded 10.0 g. (16% yield) of the title compound. The ethyl acetate solution afforded 57 g. of an oil, which was triturated under hexane. A white solid appeared. It was filtered off, giving 41.5 g. (66% yield) of the title compound, M.P. 134° C. (dec.).

Analysis: Calculated for $C_8H_{10}BrNO_5S$: C, 30.78; H, 3.23; Br, 25.60; N, 4.49; S, 10.27%. Found: C, 31.05; H, 3.24; Br, 25.54; N, 4.66; S, 10.21%.

Oxidation of 6-alpha-chloropenicillanic acid and 6-alpha-iodopenicillanic acid with potassium permanganate, according to the above procedure, affords 6-alpha-chloropenicillanic acid 1,1-dioxide and 6-alpha-iodopenicillanic acid 1,1-dioxide, respectively.

EXAMPLE 9

6-beta-Chloropenicillanic Acid 1,1-Dioxide

An oxidizing solution was prepared from 185 mg. of potassium permanganate, 0.063 ml. of 85% phosphoric acid and 5 ml. of water. This oxidizing solution was added dropwise to a solution of 150 mg. of sodium 6-beta-chloropenicillanate in 5 ml. of water at 0°–5° C., until the purple color of the potassium permanganate persisted. Approximately half of the oxidizing solution was required. At this point, the potassium permanganate color was discharged by the addition of solid sodium bisulfite, and then the reaction mixture was filtered. Ethyl acetate was added to the filtrate and the pH was adjusted to 1.8. The layers were separated and the aqueous layer was further extracted with ethyl acetate. The combined ethyl acetate layers were washed with water, dried and evaporated in vacuo to give 118 mg. of the title compound. The NMR spectrum (in $CD_3COCD_3$) showed absorption at 5.82 (d, 1H), 5.24 (d, 1H), 4.53 (s, 1H), 1.62 (s, 3H) and 1.50 (s, 3H) ppm.

The above product was dissolved in tetrahydrofuran and an equal volume of water was added. The pH was adjusted to 6.8 using dilute sodium hydroxide, the tetrahydrofuran was removed by evaporation in vacuo, and the residual aqueous solution was freeze dried. This afforded the sodium salt of the title compound.

EXAMPLE 10

6-beta-Bromopenicillanic Acid 1,1-Dioxide

To a solution of 255 mg. of sodium 6-beta-bromopenicillanate in 5 ml. of water, at 0° to 5° C., was added a solution prepared from 140 mg. of potassium permanganate, 0.11 ml. of 85% phosphoric acid and 5 ml. of water, at 0° to 5° C. The pH was maintained between 6.0 and 6.4 during the addition. The reaction mixture was stirred at pH 6.3 for 15 minutes, and then the purple solution was covered with ethyl acetate. The pH was adjusted to 1.7 and 330 mg. of sodium bisulfite was added. After 5 minutes, the layers were separated and the aqueous layer was further extracted with ethyl acetate. The combined ethyl acetate solutions were washed with brine, dried ($MgSO_4$) and evaporated in vacuo. This afforded 216 mg. of the title compound as white crystals. The NMR spectrum (in $D_2O$) showed absorptions at 5.78 (d, 1H, J=4 Hz), 5.25 (d, 1H, J=4 Hz), 4.20 (s, 1H), 1.65 (s, 3H) and 1.46 (s, 3H) ppm.

EXAMPLE 11

6-beta-Iodopenicillanic Acid 1,1-Dioxide

Oxidation of 6-beta-iodopenicillanic acid with potassium permanganate, according to the procedure of Example 10, affords 6-beta-iodopenicillanic acid, 1,1-dioxide.

EXAMPLE 12

Chloromethyl 6-alpha-bromopenicillanate 1,1-Dioxide 6-alpha-Bromopenicillanic acid 1,1-dioxide is esterified by the procedure of Example 1 to provide the title compound.

The above procedure is repeated but the chloroiodomethane used therein is replaced by an equimolar amount of bromoiodomethane, diiodomethane, di(methylsulfonyloxy)methane, di(isopropylsulfonyloxy)methane, di(isovalerylsulfonyloxy)methane or a compound of the formula $(R^2C_6H_4SO_2O)_2CH_2$ where $R^2$ is H, 3-Cl, 4-Br, 4-$NO_2$, 4-$CH_3$, 3-n-$C_3H_7$, 4-$CH_3O$, 4-$C_2H_5O$ or 3-$(CH_3)_2CH_2$ to provide, respectively:
bromomethyl 6-alpha-bromopenicillanate 1,1-dioxide,
iodomethyl 6-alpha-bromopenicillanate 1,1-dioxide,
methylsulfonyloxymethyl 6-alpha-bromopenicillanate 1,1-dioxide,
isopropylsulfonyloxymethyl 6-alpha-bromopenicillanate 1,1-dioxide,
isovalerylsulfonyloxymethyl 6-alpha-bromopenicillanate 1,1-dioxide,
and $R^2C_6H_4$-sulfonyloxymethyl 6-alpha-bromopenicillanate 1,1-dioxides where $R^2$ is as defined above.

The corresponding esters of 6-alpha-chloropenicillanic acid 1,1-dioxide; 6-alpha-iodopenicillanic acid 1,1-dioxide; 6-beta-chloropenicillanic acid 1,1-dioxide and 6-beta-iodopenicillanic acid 1,1-dioxide are prepared in like manner.

EXAMPLE 13

Chloromethyl 6-alpha-Chloropenicillanate

A mixture of 2.35 g. (0.01 mole) 6-alphachloropenicillanic acid and 5.0 ml. water is treated with 5.0 ml. 2 N potassium hydroxide. Potassium bicarbonate (6.0 g.), tetrabutylammonium hydrogen sulfate (0.34 g., 0.001 mole), dichloromethane (20 ml.) and chloromethyl chlorosulfate (1.64 g., 0.011 mole) is added and the resulting mixture stirred at 25° to 30° C. for two hours. The reaction mixture is filtered, the layers separated. The organic phase is dried ($Na_2SO_4$) and evaporated to dryness to afford the title compound.

The following compounds are made in like manner from the appropriate 6-substituted penicillanic acid:
chloromethyl 6-alpha-bromopenicillanate,
chloromethyl 6-alpha-iodopenicillanate,
chloromethyl 6-beta-chloropenicillanate,
chloromethyl 6-beta-bromopenicillanate,
chloromethyl 6-beta-iodopenicillanate
chloromethyl 6,6-dibromopenicilllanate,
chloromethyl 6,6-dichloropenicilllanate,
chloromethyl 6,6-diiodopenicillanate,
chloromethyl 6-chloro-6-iodopenicillanate,
chloromethyl 6-bromo-6-iodopenicillanate,
chloromethyl 6-bromo-6-chloropenicillanate.

EXAMPLE 14

Chloromethyl 6-alpha-chloropenicillanate 1-Oxide

To a stirred solution of 8.49 g. (0.03 mole) chloromethyl 6-alpha-chloropenicillanate in 200 ml. chloroform is added at 0° C. a solution of 6.12 g. (0.03 mole) 3-chloroperbenzoic acid in 100 ml. chloroform. Stirring is continued for 1.5 hours at 0°–5° C. The reaction mixture is then filtered, washed with sodium bicarbonate solution, water and dried ($Na_2SO_4$). Evaporation of solvent in vacuo affords the crude title compound as a mixture of alpha- and beta-sulfoxides which can be purified, if desired, by chromatography on silica gel.

Alternately, the title compound is prepared by oxidation of 6-alpha-chloropenicillanic acid by oxidation with one equivalent of 3-chloroperbenzoic acid in tetrahydrofuran at 0°–25° C. for about one hour, according to the procedure of Harrison et al., *Jour. Chem. Soc. (London), Perkin I*, 1772 (1976). The resulting 6-alpha-chloropenicillanic acid 1-oxide is then esterified by the procedure of Example 1 to provide the desired chloromethyl ester.

The remaining 6-substituted penicillanate esters and 6,6-dihalopenicillanate esters provided in Examples 1, 1B and 13 are converted to the corresponding 1-oxides by the above procedure.

The same compound is obtained by reaction of 0.1 mole chloromethyl 6-alpha-chloropenicillanate in 150 ml. isopropanol containing 0.8 ml. of 0.5 M sodium tungstate ($Na_2WO_4$) or an equivalent amount of potassium molybdate ($K_2MoO_4$) with 0.1 mole of hydrogen peroxide (30%). The peroxide is added slowly to the other reagents at 60° C., after which the mixture is allowed to cool while stirring overnight. The product is isolated as described above.

EXAMPLE 15

Chloromethyl 6-alpha-chloropenicillanate 1,1-Dioxide

To a solution of 2.83 g., 0.01 mole chloromethyl 6-alpha-chloropenicillanate in 50 ml. of chloroform is added 4.32 g. (0.025 mole) m-chloroperbenzoic acid and the mixture is stirred under a nitrogen atmosphere for 36 hours at room temperature. The solvent is evaporated in vacuo, the residue partitioned between ethyl acetate and water at pH 6.0 and sodium bisulfite is added until a test for the presence of peroxides is negative. The pH is adjusted to 8.0, the layers separated and the organic phase is washed with brine, dried ($Na_2SO_4$) and evaporated to dryness in vacuo to provide the title compound.

Alternatively, the title compound is obtained by oxidation of the same starting material in methanol or ethanol containing a catalytic amount of sodium tungstate and addition of 2 molar equivalents of hydrogen peroxide at temperatures of from 20° to 60° C.

In like manner the remaining penicillanate esters provided in Example 13 are converted to the corresponding 1,1-dioxides by the above procedures.

Similarly, the remaining chloromethyl-6-substituted (and 6,6-disubstituted) penicillanate 1-oxides provided in Example 14 are converted to 1,1-dioxides by the above procedure employing one half the amount of m-chloroperbenzoic acid, or by employing an equimolar amount of peracetic acid.

EXAMPLE 16

1,1-Dioxo-6,6-dibromopenicillanoyloxymethyl 6-(D-2-azido-2-phenylacetamido)penicillanate To a mixture of 0.232 g. (0.37 mmole) tetrabutylammonium 6-(D-2-azido-2-phenylacetamido)penicillanate* and 10 ml. acetone was added 0.20 g. (0.37 mmole) iodomethyl 6,6-dibromopenicillanate 1,1-dioxide and the mixture stirred at room temperature for 30 minutes. An additional 50 mg. of tetrabutylammonium D-(2-azido-2-phenylacetamido)penicillanate was added and stirring continued for 30 minutes. The reaction mixture was concentrated to dryness and the residue placed on a column of silica gel (50 g.). Elution with 1:1 (v/v) ethyl acetate/hexane was carried out taking 7 ml. fractions. Fractions 17-24 were combined and evaporated in vacuo to afford 0.14 g. (49%) of the desired product as a light yellow oil. $^1$H-NMR ($CDCl_3$) ppm (delta): 1.4 (s, 3H), 1.5 (s, 3H), 1.59 (s, 3H), 1.62 (s, 3H), 4.4 (s, 1H), 4.5 (s, 1H), 4.97 (s, 1H), 5.04 (s, 1H), 5.4–5.70 (m, 2H), 5.85 (s, 2H), 7.05 (d, 1H), 7.35 (s, 5H); Infrared (neat) $cm^{-1}$: 1810, 1775.

*The tetrabutylammonium salt was prepared as follows: One gram of sodium D-2-azido-2-phenylacetamido penicillanate, 50 ml. ethyl acetate and 25 ml. water, were combined and adjusted to pH 2.0 (2N HCl). The organic layer was separated, washed with brine (10 ml.) and the solvent evaporated in vacuo. The residual foam was dissolved in 30 ml. methylene chloride, 15 ml. water was added and 40% tetrabutylammonium hydroxide solution was added until the aqueous phase reached pH 8.0. The organic layer was separated, the aqueous layer extracted again with methylene chloride (2×20 ml.) and the combined extracts were dried ($Na_2SO_4$) and concentrated to dryness to afford a hard gum. This was triturated with ethyl acetate (2×10 ml.) and ethyl ether (2×10 ml.). The resulting off-white solid was air dried to afford 1.25 g. of the desired tetrabutylammonium salt.

EXAMPLE 17

1,1-Dioxo-6,6-dibromopenicillanoyloxymethyl 6-(D-2-benzyloxycarbonylamino-2-phenylacetamido)-penicillanate The title compound is obtained by employing tetrabutylammonium 6-(D-2-benzyloxycarbonylamino-2-phenylacetamido)penicillanate in place of the corresponding azidocillin salt in the procedure of Example 10.

EXAMPLE 18

1,1-Dioxo-6-bromo-6-chloropenicillanoyloxymethyl 6-[D-2-azido-2-(p-hydroxyphenyl)acetamido]penicillanate To a stirred solution of 4.29 g. (0.01 mole) potassium 6-(D-2-azido-2-p-hydroxyphenylacetamido)pencillanate in 75 ml. dimethylsulfoxide is added 4.86 g. (0.01 mole) iodomethyl 6-bromo-6-chloropenicillanate 1,1-dioxide and the mixture stirred at ambient temperature for 18 hours. The reaction mixture was poured into water, extracted with ethyl acetate, the extracts washed with water and saturated sodium chloride solution, then dried ($Na_2SO_4$). Evaporation of solvent affords the crude product which can be purified if desired by chromatography on silica gel.

When the above reaction is carried out in dimethylformamide, N-methylpyrrolidone, ethyl acetate, dichloromethane or hexamethylphosphoric acid triamide as solvent in place of dimethylsulfoxide at temperatures of from 25° to 50° C., the results are substantially the same.

EXAMPLE 19

1,1-Dioxo-6,6-dichloropenicillanoyloxymethyl 6-(D-2-azido-2-phenylacetamido)penicillanate A mixture of 3.08 g. (5 mmole) tetrabutylammonium 6-(D-2-azido-2-phenylacetamido)penicillanate, ethyl acetate 25 ml. and methylene chloride 10 ml. is stirred and a solution of 2.21 g. (5 mmole) iodomethyl 6,6-dichloropenicillanate 1,1-dioxide in 20 ml. ethyl acetate is added. The resulting mixture is stirred at room temperature for one hour, the methylene chloride evaporated in vacuo and the precipitate of tetrabutylammonium iodode is removed by filtration. Evaporation of the filtrate affords the desired product.

EXAMPLE 20

1,1-Dioxo-6-bromo-6-iodopenicillanoyloxymethyl 6-(D-2-benzyloxycarbonylamino-2-phenylacetamido)-penicillanate Sodium 6-(D-2-benzyloxycarbonylamino-2-phenylacetamido)penicillanate (4.05 g., 0.01 mole), 4-toluenesulfonyloxymethyl 6-bromo-B 6-iodopenicillanate 1,1-dioxide and 50 ml. dimethylformamide are combined and stirred at 30° C. for 24 hours. The mixture is poured into water (125 ml.), the pH adjusted to 8.5 with sodium hydroxide solution and extracted with ethyl acetate. The extract is washed with water, brine, dried ($Na_2SO_4$) and the solvent evaporated in vacuo to afford the crude title compound. It is purified by column chromatography on silica gel.

EXAMPLE 21

1,1,-Dioxo-6,6-dibromopenicillanoyloxymethyl 6-[D-2-benzyloxycarbonylamino-2-(p-hydroxyphenyl)acetamido]penicillanate To a mixture of 101.3 g. (0.25 mole) 6-[D-2-benzyloxycarbonylamino-2-(p-hydroxyphenyl)acetamido]penicillanic acid, 250 ml. water, 500 ml. methylene chloride and 84.8 g. (0.25 mole) tetrabutylammonium bisulfate at 5° C. is added 125 ml. 2 N sodium hydroxide while maintaining the mixture at 5°-10° C. The organic layer is separated and the aqueous phase extracted with methylene chloride. The combined organic layers are dried (Na$_2$SO$_4$) and solvent evaporated in vacuo. The residue is dissolved in 1000 ml. ethyl acetate, evaporated in vacuo to about 300 ml. and refrigerated overnight. The precipitated tetrabutylammonium 6-[D-2-benzyloxycarbonylamino-2-(p-hydroxyphenyl)acetamido]penicillanate is collected by filtration and dried in vacuo.

To 74.1g. (0.10 mole) tetrabutylammonium 6-[D-2-benzyloxycarbonylamino-2-(p-hydroxyphenyl)acetamido]penicillanate in 1000 ml. methylethyl ketone is added 49.8 g. (0.10 mole) methylsulfonyloxymethyl 6,6-dibromopenicillanate 1,1-dioxide and the resulting mixture stirred at 50° C. for one hour. The solvent is evaporated in vacuo and the residue partitioned between ethyl acetate and water. The aqueous layer is separated, washed with ethyl acetate and the combined organic layers washed with brine and dried (Na$_2$SO$_4$). Evaporation of ethyl acetate in vacuo affords the title compound.

EXAMPLE 22

1,1-Dioxo-6-beta-bromopenicillanoyloxymethyl 6-(D-2-azido-2-phenylacetamido)penicillanate To a mixture of 0.152 g. (0.25 mmole) tetrabutylammonium (D-2-azido-2-phenylacetamido)penicillanate and 5.0 ml. acetone was added 0.14 g. (0.25 mmole) iodomethyl 6-beta-bromopenicillanate 1,1-dioxide. The resulting colorless mixture was stirred at room temperature for 30 minutes, the solvent evaporated in vacuo and the residue chromatographed on a column of silica gel (25 g.), eluting with 1:1 (v/v) ethyl acetate/hexane. Fractions of 6 ml. were taken at about 30 second intervals. Fractions 13–17 were combined and concentrated in vacuo to afford 0.125 g. of the desired product as a foam. $^1$H-NMR (CDCl$_3$) ppm (delta): 1.4 (s, 3H), 1.5 (s, 3H), 1.6 (s, 3H), 1.65 (s, 3H), 4.42 (s, 1H), 4.5 (s, 1H), 4.75 (d, 1H), 5.07 (s, 1H), 5.3 (d, 1H), 5.4–5.75 (m, 2H), 5.85 (s, broad, 2H), 7.1 (d, 1H), 7.35 (s, 5H); Infrared (neat) cm$^{-1}$: 1800, 1775.

EXAMPLE 23

1,1-Dioxo-6-alpha-bromopenicillanoyloxymethyl 6-(D-2-azido-2-phenylacetamido)penicillanate A mixture of 0.308 g. (0.5 mmole) tetrabutylammonium (D-2-azido-2-phenylacetamido)penicillanate, 0.219 g. (0.485 mmole) iodomethyl 6-alpha-bromopenicillanate 1,1-dioxide and 10 ml. acetone was stirred for 30 minutes at room temperature. The solvent was evaporated in vacuo and the residue chromatographed on a column of 50 g. silica gel, eluting with 1:1 (v/v) ethyl acetate/hexane. The product-containing fractions were combined and the solvent evaporated in vacuo to afford 0.125 g. (38%) of the title compound as an oil. $^1$H-NMR (CDCl$_3$) ppm (delta): 1.43 (s, 3H), 1.5 (s, 3H), 1.6 (s, 3H), 1.66 (s, 3H), 4.4 (s, 2H), 4.64 (d, 1H), 5.05 (s, 1H), 5.1 (d, 1H), 5.4–5.7 (m, 2H), 5.85 (s, 2H), 7.08 (d, 1H), 7.35 (s, 5H); Infrared (neat) cm$^{-1}$: 1795, 1775.

EXAMPLE 24

Employing the halomethyl, alkylsulfonyloxymethyl or arylsulfonyloxymethyl esters of 6,6-dihalopenicillanic acid 1,1-dioxides or the corresponding 6-halo compounds provided in Examples 2 through 8, 12, 13 and 15 as starting material, the following compounds are prepared by the methods of Examples 16 through 23.

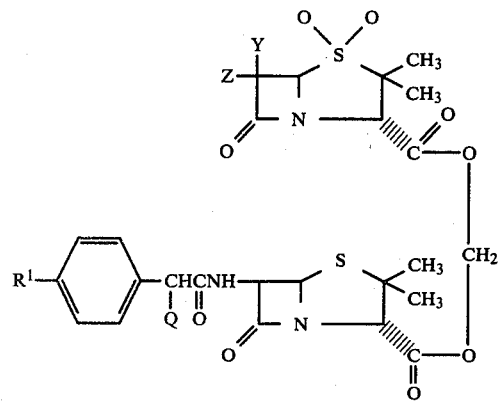

where Q, R$^1$, Y and Z are as defined below.

| Q | R$^1$ | Y | Z |
|---|---|---|---|
| 4-Cl—C$_6$H$_5$CH$_2$OCONH— | H | Cl | Cl |
| C$_6$H$_5$CH$_2$OCONH— | H | Cl | Br |
| 3-BrC$_6$H$_4$CH$_2$OCONH— | H | Br | Br |
| 4-NO$_2$C$_6$H$_4$CH$_2$OCONH— | H | Br | I |
| 2-CH$_3$C$_6$H$_4$CH$_2$OCONH— | H | I | I |
| 4-CH$_3$OC$_6$H$_4$CH$_2$OCONH— | HO | Cl | Cl |
| C$_6$H$_5$CH$_2$OCONH— | HO | Cl | Br |
| 3-CH$_3$OC$_6$H$_4$CH$_2$OCONH— | HO | Br | Br |
| 2-ClC$_6$H$_4$CH$_2$OCONH— | HO | Br | I |
| C$_6$H$_5$CH$_2$OCONH— | HO | H | alpha-I |
| N$_3$ | HO | H | alpha-Br |
| C$_6$H$_5$CH$_2$OCONH— | H | H | alpha-Cl |
| 4-NO$_2$C$_6$H$_4$CH$_2$OCONH— | HO | H | beta-I |
| N$_3$ | HO | H | beta-Br |
| N$_3$ | H | H | beta-Cl |

EXAMPLE 25

1,1-Dioxopenicillanoyloxymethyl 6-(D-2-amino-2-phenylacetamido)penicillanate A mixture of 1.2 g. 5% palladium-on-calcium carbonate and 30 ml. 1:1 by volume isopropanol/methylene chloride was hydrogenated at 50 psi (3.52 kg./cm.$^2$) for 30 minutes. To this was added 0.25 g. (0.32 mmole) 1,1-dioxo 6,6-dibromopenicillanoyloxymethyl 6-(D-2-azido-2-phenylacetamido)penicillanate dissolved in 3 ml. methylene chloride. The resulting mixture was hydrogenated at 50 psi for one hour. The catalyst was removed by filtration, washing with 30 ml. 1:1 isopropanol/methylene chloride. The filtrate was concentrated in vacuo to afford a tan solid. This was triturated with 15 ml. ethyl ether, filtered, washed with 10 ml. ether and air dried to afford 0.195 g. of product. $^1$H-NMR (CDCL$_3$) ppm (delta): 1.5 (d, 6H), 1.6 (d, 6H), 3.55 (d, 2H), 4.45 (s, 1H), 4.55 (s, 1H), 4.6–4.75 (m, 2H), 5.5–5.7 (m, 2H), 5.9 (q, 2H), 7.4 (s, 4H), 8.1 (d, 1H).

EXAMPLE 26

1,1-Dioxopenicillanoyloxymethyl 6-(D-2-amino-2-phenylacetamido)penicillanate hydrobromide A mixture of 0.125 g. (0.17 mmole) 1,1-dioxo-6-alpha-bromopenicillanoyloxymethyl 6-(D-2-azido-2-phenylacetamido)penicillanate, 10 ml. methylene chloride, 10 ml. isopropanol and 0.35 g. 10% palladium-on-carbon was hydrogenated at 50 psi (3.52 kg./cm.$^2$) for 75 minutes. The catalyst was removed by filtration and the filtrate evaporated in vacuo to afford an off-white solid residue. This was triturated with ethyl ether, filtered, washing with ether and the product dried under a nitrogen atmosphere to afford 78 mg. of the title compound. The infrared spectrum and $^1$H-NMR spectrum in dimethylsulfoxide (D$_6$) were identical to those of an authentic sample.

Hydrogenation of 100 mg. of 1,1-dioxo-6-beta-bromopenicillanoyloxymethyl 6-(D-2-azido-2-phenylacetamido)penicillanate for one hour by the above procedure gave 68 mg. of the same product.

EXAMPLE 27

1,1-Dioxopenicillanoyloxymethyl 6-[D-2-amino-2-(p-hydroxyphenyl)acetamido]penicillanate A mixture of 1.0 g. 1,1-dioxo-6-bromo-6-chloropenicillanoyloxymethyl 6-[D-2-azido-2-(p-hydroxyphenyl)acetamido]penicillanate, 50 ml. methylene chloride, 50 ml. isopropanol, 270 mg. triethylamine and 1 g. 5% palladium-on-carbon catalyst is shaken with hydrogen at 60 psi (4.2 kg./cm.$^2$) for two hours. The catalyst is removed by filtration and the filtrate washed with 3×50 ml. water. The washings are combined, adjusted to pH 7.5 and extracted with methylene chloride. The combined organic layers are dried (MgSO$_4$) and the solvent evaporated in vacuo to afford the crude title compound which is purified by chromatography on silica gel.

EXAMPLE 28

1,1-Dioxopenicillanoyloxymethyl 6-(D-2-amino-2-phenylacetamido)penicillanate

A. A mixture of 2.5 g. 1,1-dioxo-6,6-dichloropenicillanoyloxymethyl 6-(D-2-azido-2-phenylacetamido)-penicillanate, 60 ml. ethyl acetate, 20 ml. 5% (w/v) sodium bicarbonate solution and 2.5 g. of 10% palladium-on-carbon catalyst is hydrogenated with agitation at 50 psi (3.5 kg./cm.$^2$) until hydrogen uptake ceases. The catalyst is removed by filtration, the layers separated and the aqueous phase extracted with ethyl acetate. The combined organic layers are dried (Na$_2$SO$_4$) and evaporated in vacuo to provide the desired product. It is purified by chromatography on silica gel.

When the palladium catalyst employed above is replaced by a similar amount of nickel, platinum or rhodium catalyst similar results are obtained.

B. A mixture of 3.0 g. 1,1-dioxo-6-bromo-6-iodopenicillanoyloxymethyl 6-(D-2-azido-2-phenylacetamido)penicillanate, 75 ml. glacial acetic acid, 1.5 g. sodium acetate and one gram of 5% rhodium-on-carbon catalyst is hydrogenated at three atmospheres pressure. When hydrogen uptake is complete the mixture is filtered, the filtrate evaporated in vacuo, and the residue taken up in ethyl acetate and washed with water. The organic layer is dried (Na$_2$SO$_4$) and evaporated to dryness in vacuo to afford the desired product.

C. Hydrogenation of 1,1-dioxo-6,6-dibromopenicillanoyloxymethyl 6-(D-2-benzyloxycarbonylamino-2-phenylacetamido)penicillanate by the above procedures affords the same product.

EXAMPLE 29

Hydrogenation of the compounds provided in Examples 16-24 by the procedures of Examples 25 through 28 affords compounds of the formula below in like manner

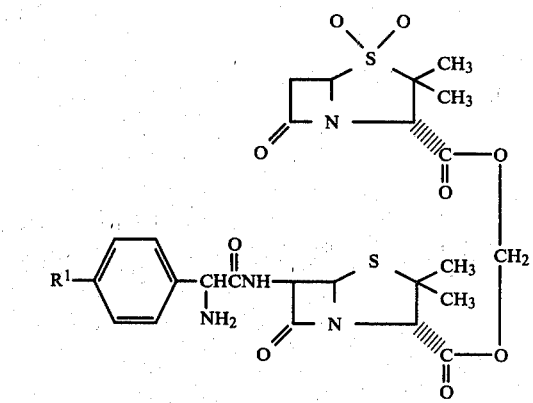

where R$^1$ is as defined in Examples 16 through 24.

PREPARATION A

6-[D-2-azido-2-(p-hydroxyphenyl)acetamido]penicillanic Acid

The method is that of Japanese Kokai No. 78-37,691; Chem. Abstr., 89, 109466v (1978).

To a mixture of 10 g. 6-aminopenicillanic acid and 100 ml. acetone is added dropwise at 0° C. 10 g. D-2-azido-2-(p-hydroxyphenyl)acetic acid chloride while simultaneously adding powdered potassium bicarbonate to maintain the mixture at pH 7–8. After the addition is complete the mixture is stirred at room temperature and pH 7–8 for five hours. The reaction mixture is filtered and the filtrate evaporated in vacuo. The residue is purified by chromatography on silica gel to afford the title compound.

PREPARATION B 6,6-Dibromopenicillanic Acid

To 500 ml. of dichloromethane cooled to 5° C. was added 119.9 g. of bromine, 200 ml. of 2.5 N sulfuric acid and 34.5 g. of sodium nitrite. To this stirred mixture was then added 54.0 g. of 6-aminopenicillanic acid, portionwise over 30 minutes, with the temperature maintained from 4° to 10° C. Stirring was continued for 30 minutes at 5° C., and then 410 ml. of a 1.0 M solution of sodium bisulfite was added dropwise at 5° to 10° C. during 20 minutes. The layers were separated and the aqueous layer was extracted twice with 150 ml. of dichloromethane. The original dichloromethane layer was combined with the two extracts to give a solution of 6,6-dibromopenicillanic acid. This solution was used directly in preparation of esters or evaporated to dryness to provide the desired product.

PREPARATION C

6-Chloro-6-iodopenicillanic Acid

To 100 ml. of dichloromethane cooled to 3° C. was added 4.87 g. of iodine chloride, 10 ml. of 2.5 N sulfuric acid and 2.76 g. of sodium nitrite. To this stirred mixture was then added 4.32 g. of 6-aminopenicillanic acid portionwise during a 15 minute period. Stirring was continued for 20 minutes at 0°–5° C., and then 100 ml. of 10% sodium bisulfite solution was added dropwise at ca. 4° C. Stirring was continued for 5 minutes and the the layers were separated. The aqueous layer was extracted with dichloromethane (2×50 ml.) and the combined dichloromethane solutions were washed with brine, dried (MgSO4) and evaporated in vacuo to give the title compound as a tan solid, m.p. 148°–152° C. The NMR spectrum of the product (CDCl3) showed absorptions at 5.40 (s, 1H), 4.56 (s, 1H), 1.67 (s, 3H) and 1.50 (s, 3H) ppm. The IR spectrum (KBr disc) showed absorptions at 1780 and 1715 cm$^{-1}$.

PREPARATION D

6-Bromo-6-iodopenicillanic Acid

To 100 ml. of dichloromethane, cooled to 5° C., was added 10 ml. of 2.5 N sulfuric acid, 6.21 g. of iodine bromide and 2.76 g. of sodium nitrite. To this mixture was added, with vigorous stirring, at 0°–5° C., over 15 minutes, 4.32 g. of 6-aminopenicillanic acid. Stirring was continued for a further 20 minutes at 0°–5° C., and then 100 ml. of 10% sodium bisulfite was added dropwise between 0° and 10° C. At this point, the layers were separated and the aqueous layer was extracted with dichloromethane (3×50 ml.). The combined dichloromethane layers were washed with brine, dried (MgSO4) and evaporated in vacuo. The residue was dried under high vacuum for 30 minutes to give 6.0 g. (72% yield) of the title compound m.p. 144°–147° C. The NMR spectrum (CDCl3) showed absorptions at 5.50 (s, 1H), 4.53 (s, 1H), 1.70 (s, 3H) and 1.53 (s, 3H) ppm. The IR spectrum (KBr disc) showed absorptions at 1785 and 1710 cm$^{-1}$. The mass spectrum showed a prominent ion at m/e=406.

PREPARATION E

6-Chloro-6-bromopenicillanic Acid

6-Chloro-6-bromopenicillanic acid is prepared from 6-aminopenicillanic acid via diazotization followed by reaction with bromine chloride, according to the procedure of Preparation D.

I claim:

1. A compound of the formula

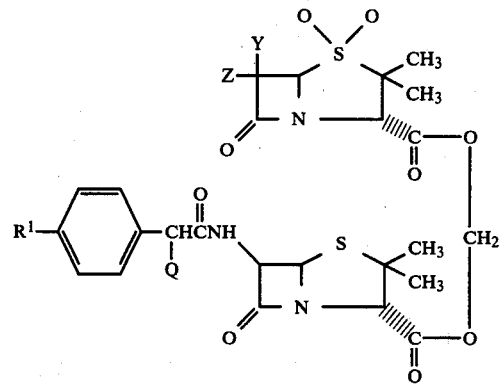

wherein
R$^1$ is H or OH;
Y and Z are each Cl, Br or I, or Y is H and Z is Cl, Br or I and
Q is N$_3$ or NHCO$_2$CH$_2$C$_6$H$_4$R$^4$ where R$^4$ is H, Cl, Br, NO$_2$, CH$_3$ or OCH$_3$.

2. A compound according to claim 1 wherein Y and Z are each Cl or Br, or Y is H and Z is Cl or Br.

3. A compound according to claim 2 wherein Y and Z are each Br or Y is H and Z is Br.

4. A compound according to claim 3 wherein Y and Z are each Br.

5. A compound according to claim 1 wherein Q is N$_3$ or NHCO$_2$CH$_2$C$_6$H$_5$.

6. A compound according to claim 5 wherein Q is N$_3$.

7. A compound according to claim 6 wherein R$^1$ is H, Y is H and Z is Br.

8. The compound according to claim 6 wherein R$^1$ is H, and Y and Z are each Br.

9. A compound according to claim 6 wherein R$^1$ is HO, Y is H and Z is Br.

10. The compound according to claim 6 wherein R$^1$ is HO, Y and Z are each Br.

* * * * *